United States Patent [19]

Berthold

[11] 4,128,579

[45] Dec. 5, 1978

[54] PROCESS FOR THE MANUFACTURE OF α,β-UNSATURATED CYCLOALIPHATIC KETOXIMES

[75] Inventor: Rüdiger Berthold, Bad Soden am Taunus, Fed. Rep. of Germany

[73] Assignee: Hoechst Aktiengesellschaft, Frankfurt am Main, Fed. Rep. of Germany

[21] Appl. No.: 856,738

[22] Filed: Dec. 1, 1977

[30] Foreign Application Priority Data

Dec. 3, 1976 [DE] Fed. Rep. of Germany ....... 2654851

[51] Int. Cl.$^2$ .......................................... C07C 131/08
[52] U.S. Cl. ................................. 260/566 A
[58] Field of Search ..................... 260/566 A

[56] References Cited

PUBLICATIONS

Houben-Weyl, "Methoden der Organischen Chemie, vol. X/4 pp. 80-82; vol. X/1 1112.
Annalen, vol. 330 p. 191 (1904).
Berichite, vol. 31 p. 1383 (1898).
Koevenagel, Annalen, vol. 281 p. 112 (1894).
Montgomery et al., J. Org. Chem. vol. 17 p. 823 (1952).

Primary Examiner—Gerald A. Schwartz
Attorney, Agent, or Firm—Curtis, Morris & Safford

[57] ABSTRACT

α,β-Unsaturated cycloaliphatic ketoximes and their salts are obtained in high purity and yield by reacting an α,β-unsaturated cycloaliphatic ketone with hydroxylamine hydrochloride, sulfate or hydrogen sulfate in water in a pH range of 0 to 4.5. The products are intermediates for aromatic amines.

9 Claims, No Drawings

PROCESS FOR THE MANUFACTURE OF α,β-UNSATURATED CYCLOALIPHATIC KETOXIMES

The reaction of hydroxylamine with α,β-unsaturated keto compounds can take several directions: β-hydroxylaminoketones, β-hydroxylamino-oximes and various oxazole derivatives can be formed in addition to α,β-unsaturated oximes (Houben-Weyl, Methoden der organischen Chemie [Methods of Organic Chemistry], volume X/4, 80 to 81). The recommended best method for the manufacture of α,β-unsaturated oximes is to leave equimolar amounts of ketone and hydroxylamine hydrochloride in methanol solution to stand at room temperature. In the original literature cited there (Annalen 330 (1904) 191), 3 to 4 days are mentioned as the reaction time. Such a process is obviously unsuitable for an industrial operation. Apart from the long reaction time, the solubility of hydroxylamine hydrochloride in methanol is very low (in other work by the same author, Ber. 31 (1898) 1384, 1.25 liters of methanol are employed per mole of ketone). Apart from the completely unacceptable space-time yield, the solvent must be reprocessed.

In the quoted reference, Annalen 330, 191, it is stated that, in the reaction with hydroxylamine hydrochloride in methanol, an addition to the C—C double bond is avoided in the cases where such an addition readily takes place with free hydroxylamine. It is mentioned, however, that there are exceptions to this rule and that, for example, a simple oxime is not obtained in the case of phorone.

The manufacture of cycloaliphatic ketoximes in a neutral aqueous-ethanolic medium has likewise already been described. In this case, hydroxylamine hydrochloride is employed initially, but a neutral reaction is then produced by the addition of sodium carbonate solution or potassium hydroxide solution and ethanol is added subsequently until the solution becomes clear. Here also, reaction times of 2 to 8 days are indicated (Annalen 281 (1894), 112; J. org. Chem. 17 (1952) 823). On the other hand, it is known from the literature that free hydroxylamine promotes the formation of hydroxylamino-oximes (Houben-Weyl, volume X/4, 82; volume X/1, 1112). Thus, it is mentioned that in the case of carvone the addition of hydroxylamine to the double bond takes place 30 times faster than the formation of oxime.

The relevant literature thus does not provide any general teaching as to how α,β-unsaturated cycloaliphatic ketoximes are obtained free from by-products.

It has now been found that an α,β-unsaturated cycloaliphatic ketoxime or a salt thereof is obtained from an α,β-unsaturated cycloaliphatic ketone and hydroxylamine hydrochloride, or hydroxylamine bisulphate or sulphate, in good yield and high purity, if the reaction is carried out in the pH range from 0 to 4.5, preferably 0 to 2.5, especially from 0 to 1.5.

To carry out the reaction, for example, an aqueous solution of excess hydroxylamine hydrochloride, or hydroxylamine bisulphate or sulphate, and the ketone are initially introduced and bases, for example sodium hydroxide solution, sodium carbonate or sodium acetate, are added at temperatures from about −10° to 110° C., preferably from 0° C. up to the boiling point of the reaction mixture, in particular at 20 to 70° C., in such a manner that the indicated pH range is maintained.

Since hydroxylamine (bi)sulphate and especially hydroxylamine hydrochloride are expensive, they can also be used in an equivalent amount or in only a slight excess. To maintain the acid pH range and an acceptable reaction time, it is then advisable, however, initially to introduce salts of strong acids with weak bases, for example ammonium salts of mineral acids, such as ammonium chloride, ammonium sulphate, mono- or tri-methylammonium chloride, together with the hydroxylamine hydrochloride or hydroxylamine bisulphate or sulphate.

Depending on the pH range selected for the reaction, the free ketoxime or its hydrochloride or (bi)sulphate, or in some cases also mixtures, are obtained. If the ketoxime salt is desired, an addition of the corresponding acid, for example of hydrochloric acid, can be appropriate in order to repress the hydrolysis of the oxime salts completely.

It is stated in Annalen 330 (1904) 191 that oxime hydrochlorides can frequently be decomposed by water and that, in the case of terpene-ketones, the free oximes are separated out by pouring the reaction mixture into water. It is therefore surprising that, according to the invention, the oxime salts are also obtainable. With respect to the methods, indicated in the literature cited above, for the manufacture of ketoximes in an "acid" medium it must be taken into account that in those methods methanol was used as the organic solvent and that the reaction of the ketones in that case evidently takes place with the undissociated hydroxylammonium chloride. Moreover, since a pH of 4.7 is indicated as the optimum for oximation reactions in Weygand-Hilgetag, Organisch-chemische Experimentierkunst [The Art of Experimentation in Organic Chemistry], 3rd edition, 1964, page 580, it is surprising that the reaction according to the invention proceeds at very low pH values - down to 0.

The process according to the invention gives the free ketoximes or the salts thereof in good yields without by-products, such as hydroxyamino-oximes or hydroxylamino-ketones. Due to the high solubility of hydroxylamine hydrochloride, or hydroxylamine bisulphate or sulphate, the space yield can be increased to up to 15 moles of oxime per liter of water. Since, furthermore, the reaction times are fairly short and extend to about 10 to 60 minutes depending on the reaction temperature, the space-time yields are also high.

To work up the reaction mixture, the precipitated ketoxime salt can be isolated by centrifuging or filtration. Although more than half of the product then remains in the mother liquor, the latter can be recycled into the process so that the result is a quantative yield of oxime. A very pure ketoxime salt is obtained when the oximation is carried out with an addition of neutral salts, such as, for example, sodium chloride, and the oxime salt is washed with the corresponding salt solution. Since this salt-containing mother liquor can also be recycled into the process, the effluent load is small. If the free ketoxime is desired, the reaction is advantageously carried out in such a way that the pH value is in the upper range according to the invention towards the end of the reaction.

Ketones having a 5-membered to 8-membered ring are preferred as the starting ketones, and these can carry lower alkyl groups, lower alkenyl groups or phenyl groups as substituents. The double bond conjugated with the keto group is preferably in the ring. Examples of suitable starting materials are carvone, carvenone, isophorone, 3-methyl-5-phenyl-cyclohex-2-en-1-one, 5-methyl-cyclohex-2-en-1-one and 3,5-dimethy-cyclohex-2-en-1-one.

The products of the process are known and are intermediate products for the manufacture of aromatic amines (Houben-Weyl, Methoden der organischen Chemie [Methods of Organic Chemistry], volume 10/4 (1968) 265; Krauch-Kunz, Reaktionen der organischen Chemie [Reactions of Organic Chemistry], 5th edition, 585; Organic Reactions, volume 11, 1).

In the examples which follow, the precentage data are by weight.

EXAMPLE 1

309 g of hydroxylamine hydrochloride, 99% pure, (= 4.4 moles) are dissolved in 400 ml of water.

After 502 g of 3,5-dimethylcyclohex-2-enone, 99% pure, (= 4.0 moles) have been added, 362 ml of 33% strength sodium hydroxide solution are allowed to run in in such a manner that the pH value does not exceed 2.5. During this procedure, the temperature rises from about 40° C. to 65° C. At the end, the mixture is stirred at 70° C. for a further 30 minutes, and during this time the pH value can rise up to 4.5.

In a heatable separating funnel the hot solution separates into an aqueous phase and liquid 3,5-dimethylcyclohex-2-enone oxime.

545 g are obtained, that is to say 98% of theory. The content of pure compound, determined by gas chromatography, is more than 99%.

EXAMPLE 2

50 ml of concentrated hydrochloric acid and 150 g of hydroxylamine hydrochloride, 99% pure, (2.16 moles) are added to 300 ml of 20% strength sodium chloride solution. After warming to 50° C., 250 g of 3,5-dimethylcyclohex-2-enone, 99% pure, (2 moles) are added all at once. In the course of 15 minutes, the temperature now rises to about 75° C. due to the heat of reaction. The mixture is stirred at this temperature for about a further 30 minutes and is then cooled slowly to +5° C. A thick paste is thus formed. After filtration and washing of the filter cake with sodium chloride solution, 378 g of 3,5-dimethylcyclohex-2-enone oxime hydrochloride (1.94 moles), that is to say 97% of theory, are obtained with a content of pure compound of ~90%.

EXAMPLE 3

20 ml of concentrated hydrochloric acid and 150 g of hydroxylamine hydrochloride are added to 250 ml of mother liquor which was formed in the reaction of hydroxylamine hydrochloride and 5-methyl-cyclohex-2-enone in water. After warming to 40° C., 222 g of 5-methylcyclohexenone, 99% pure, (2 moles) are added and the mixture is thoroughly stirred. In the course of 20 minutes, the temperature rises to about 65° C. and a clear solution is formed. Stirring is continued for 1 hour, the temperature falling again and the reaction product gradually crystallizing out.

After stirring for 1 hour at +5° C., the precipitated 5-methylcyclohexenone oxime hydrochloride is filtered off.

This gives: 321 g, a content of pure compound of 98%, that is to say 97.5% of theory.

EXAMPLE 4

375 g of 3,5-dimethylcyclohexenone, 99% pure, (= 372 g of 100% pure product = 3 moles) are added to 1,080 g (= 923 ml) of a 25% strength technical grade hydroxylamine sulphate solution (d = 1.17) which additionally contains about 20 g of sulphuric acid and 20 g of ammonium sulphate, the mixture is heated to 70° C. and stirred at this temperature for one hour. The resulting solution can be worked up as follows: (a) 300 g of sodium chloride are added to the hot solution at 70° C. and the mixture is stirred without cooling until the temperature has reached 20° C. 3,5-Dimethylcyclohexenone oxime hydrochloride thus precipitates. It is filtered off and washed with 20% strength sodium chloride solution. After drying, this gives 600 g of hydrochloride with a content of pure compound of 85.1%, corresponding to 97% of theory. (b) After cooling the hot solution from 70° C. to 20° C., the latter is exhaustively extracted with an extracting agent, for example methylene chloride. The solvent is distilled off. A brown oil remains which consists of a mixture of oxime and oxime sulphate in a ratio of 2:1; yield 95%. (c) After cooling the hot solution from 70° C. to +10° C., the pH value is adjusted at this temperature to 5–5.5 with sodium hydroxide solution. This gives a thick white precipitate of 3,5-dimethylcyclohexenone oxime. It is filtered off and washed with water. This gives 510.4 g of oxime with a content of pure compound of 98%, corresponding to 95% of theory.

I claim:

1. In a process for preparing α,β-unsaturated cycloaliphatic ketoximes and their hydrochlorides, sulfates or hydrogensulfates by reaching α,β-unsaturated cycloaliphatic ketones with hydroxyl amine hydrochloride or sulfate or hydrogensulfate the improvement comprising conducting the reaction in water in a pH range of 0 to 4.5.

2. A process as claimed in claim 1, wherein the pH range is 0 to 2.5.

3. A process as claimed in claim 1, wherein the pH range is 0 to 1.5.

4. A process as claimed in claim 1, wherein the reaction is performed at a temperature of −10 to 110° C.

5. A process as claimed in claim 1, wherein the reaction is performed at a temperature of 20° to 70° C.

6. A process as claimed in claim 1, wherein stoichiometric amounts or a slight excess of said hydroxyl amine salts are reacted and the pH is controlled by adding a salt of a strong acid and a weak base.

7. A process as claimed in claim 1, wherein said cycloaliphatic ketone has 5 to 8 ring members.

8. A process as claimed in claim 1, wherein said cycloaliphatic ketone is a cycloalkenone of 5 to 8 ring carbon atoms, having in the ring a carbon-carbon double bond in conjugation to the keto group, the cycloaliphatic ring being unsubstituted or substituted by lower alkyl, lower alkenyl or phenyl.

9. A process as claimed in claim 1, wherein said ketone is carvone, carvenone, isophorone, 3-methyl-5-phenyl-cyclohex-2-en-1-one, 5-methyl-cyclohex-2-en-1-one or 3,5-dimethyl-cyclohex-2-en-1-one.

* * * * *